(12) United States Patent
Monniaux-Jaudet et al.

(10) Patent No.: US 8,758,219 B2
(45) Date of Patent: Jun. 24, 2014

(54) METHOD TO SELECT ANIMALS WITH A HIGH CAPACITY OF EMBRYO PRODUCTION

(75) Inventors: Danielle Monniaux-Jaudet, Nazelles-Negron (FR); Stéphane Fabre, Nouzilly (FR); Rozenn Dalbies-Tran, Tours (FR)

(73) Assignee: Institut National de la Recherche Agronomique, Paris (FR)

( * ) Notice: Subject to any disclaimer, the term of this patent is extended or adjusted under 35 U.S.C. 154(b) by 345 days.

(21) Appl. No.: 13/140,394

(22) PCT Filed: Dec. 18, 2009

(86) PCT No.: PCT/EP2009/067519
§ 371 (c)(1),
(2), (4) Date: Jul. 22, 2011

(87) PCT Pub. No.: WO2010/070095
PCT Pub. Date: Jun. 24, 2010

(65) Prior Publication Data
US 2011/0275886 A1    Nov. 10, 2011

(30) Foreign Application Priority Data
Dec. 19, 2008 (EP) .................................... 08291217

(51) Int. Cl.
*A61D 19/04*        (2006.01)
(52) U.S. Cl.
USPC .......................................................... 600/34
(58) Field of Classification Search
USPC ................ 600/33–35; 128/897–899
See application file for complete search history.

(56) References Cited

FOREIGN PATENT DOCUMENTS

| EP | 2368121 | 9/2011 |
|---|---|---|
| WO | WO 03/016514 | 2/2003 |

OTHER PUBLICATIONS

Monniaux et al. (Jun. 30, 2010) "Anti-Müllerian Hormone, an Endocrine Predictor of the Response to Ovarian Stimulation in the Bovine Species," *Gynécologie Obstétrique & Fertilité* 38(7-8):465-470.
Extended Search report for EP application 0829127.1 dated Apr. 9, 2009.
Blondin et al. (1996) "Superovulation can Reduce the Developmental Competence of Bovine Embryos," *Theriogenology* 46:1191-1203.
Callesen et al. (1995) "Factors Affecting the Developmental Stage of Embryos Recovered on day 7 from Superovulated Dairy Cattle," *J. Anim. Sci.* 73:1539-1543.
Durocher et al. (2006) "Effect of Hormonal Stimulation on Bovine Follicular Response and Oocyte Developmental Competence in a Commercial Operation," *Theriogenology* 65:102-115.

(Continued)

*Primary Examiner* — Charles A Marmor, II
*Assistant Examiner* — Shannon McBride
(74) *Attorney, Agent, or Firm* — Lathrop & Gage LLP (57) ABSTRACT

The present invention provides a method to select a non-human female animal subject having the capacity to produce appropriate number of transferable embryos or fertilizable oocytes in said animal, said method comprising the determination of the anti-Mullerian hormone concentration in a biological sample before an ovarian superovulatory treatment. The present invention is further directed to the use of AMH as a predictive marker of number of transferable embryos or fertilizable oocytes able to be produced in a non-human female animal.

17 Claims, 5 Drawing Sheets

(56) References Cited

OTHER PUBLICATIONS

Fanchin et al. (May 2007) "Anti-Müllerian Hormone Concentrations in the Follicular Fluid of the Preovulatory Follicle are Predictive of the Implantation Potential of the Ensuing Embryo Obtained by in Vitro Fertilization," *J. Clin. Endocrin. Metab.* 92(5):1796-1802.

Greve et al. (2001) "Rendez-vous in the Oviduct: Implications for Superovulation and Embryo Transfer," *Reprod. Nutr. Dev.* 41:451-459.

International Search Report, Written Opinion and International Preliminary Report on Patentability, Corresponding to International Application No. PCT/EP2009/067519, mailed Mar. 23, 2010 and Jun. 21, 2011.

Ireland et al. (Apr. 27, 2007) "Follicle Numbers are Highly Repeatable within Individual Animals but are Inversely Correlated with FSH Concentrations and the Proportion of Good-Quality Embryos After Ovarian Stimulation in Cattle," *Human Reprod.* 22(6):1687-1695.

Kawamata, M. (1994) "Relationships Between the Number of Small Follicles Prior to Superovulatory Treatment and Superovulatory Response in Holstein Cows," *J. Vet. Med. Sci.* 56:965-967.

Lonergan et al. (Feb. 2005) "Effect of Follicle Size on Bovine Oocyte Quality and Developmental Competence Following Maturation, Fertilization, and Culture in Vitro," *Mol. Reprod. Dev.* 37:48-53.

Mapletoft et al. (2002) "Recent Advances in the Superovulation in Cattle," *Reprod. Nutr. Dev.* 42:601-611.

Monniaux et al. (Web Release Apr. 30, 2008) "Intrafollicular Steroids and Anti-Mullerian Hormone During Normal and Cystic Ovarian Follicular Development in the Cow," *Biol. Reprod.* 79:387-396.

Monniaux et al. (Dec. 2011) "Anti-Müllerian Hormone as a Predictive Endocrine Marker for Embryo Production in the Goat," *Reproduction* 142:845-854.

Monniaux et al. (2010) "Anti-Müllerian Hormone: A Predictive Marker of Embryo Production in Cattle," *Reprod. Fertil. Dev.* 22:1083-1091.

Nelson et al. (Apr. 2009) "Anti-Müllerian Hormone-Based Approach to Controlled Ovarian Stimulation for Assisted Conception," *Human Reprod.* 24(4)867-875.

Rico et al. (Aug. 10, 2008) "Anti-Mullerian Hormone Is an Endocrine Marker of Ovarian Gonadotropin-Responsive Follicles and Can Help to Predict Superovulatory Responses in the Cow" *Biology of Reproduction* 80(1):50-59.

Takahashi et al. (1986) "The Ontogeny of Mullerian Inhibiting Substance in Granulosa Cells of the Bovine Ovarian Follicle," *Biol. Reprod.* 35:447-453.

Vigier et al. (1984) "Production of Anti-Müllerian Hormone: Another Homology between Sertoli and Granulosa Cells," *Endocrinology* 114(4):1315-1320.

METHOD TO SELECT ANIMALS WITH A HIGH CAPACITY OF EMBRYO PRODUCTION

CROSS-REFERENCE TO RELATED APPLICATIONS

This application is a U.S. National Stage application of international application PCT/EP2009/067519, filed in English on Dec. 18, 2009, which designates the United States, and which claims the benefit of EP 08291217.1, filed in English on Dec. 19, 2008. Each of these applications is incorporated by reference herein in its entirety.

The invention relates to a method to select a non-human female animal subject having the capacity to produce appropriate number of embryos or fertilizable oocytes.

In cattle, Multiple Ovulation and Embryo Transfer (MOET) programs have become a large international business. Embryo transfer has become a useful tool to accelerate the genetic progress and a national and international diffusion thereof. The technology is well established and participates to genetic selection strategies and crossbreeding schemes to improve zootechnical characteristics of dairy and beef breeds by enabling to amplify the lineage of chosen females. More than 500,000 embryos are produced annually from superovulated (FSH-stimulated) cows worldwide. Currently, more than 90% of future bull reproducers subjected to testing are produced by MOET technology. However, the number of transferable embryos (around 6 per superovulated donor cow) has not changed markedly in the last twenty years and the use of MOET technology in the animal industries is approaching a plateau. In fact, about 20% of cows don't produce any embryo after superovulatory treatments and embryo production rate is also very variable between individuals and difficult to predict. The absence of prevision of the capacity of a female animal to produce embryos induces supplementary cost in the management of selection schemes (unnecessary mobilization of technicians for animals producing low numbers of transferable embryos) and reduces the possible use of related techniques to embryo transfer such as embryo sexing.

Currently, the count of antral follicles by ovarian ultrasonography is the only method to select foreword "good donors of embryos" in a cattle herd (Durocher et al., 2006, Theriogenology 65: 102-115; Kawamata, 1994, J Vet Med Sci 56: 965-967). This method consists in transrectal ultrasonography. It needs the simultaneous presence of 2 competent experimenters for acquisition of ovarian images and requires special equipments for acquisition and treatment of video images. Moreover, the number of antral follicles in ovaries is subjected to cyclic variations with time (2 to 4 follicular waves can be observed during a 21-day sexual cycle in cow) that makes it more difficult to interpret obtained results. Therefore, since a long time, skilled person is searching for an easy and effective method to select the female animals that can produce appropriate number of embryos or fertilizable oocytes.

Recently, attention has been focused on the anti-Mullerian hormone (AMH) in the context of treatment of anovulatory infertility in woman. Numerous clinical studies have shown that AMH is the best endocrine marker of the ovarian follicular reserve in human. WO 03/016514 reported a method for predicting and monitoring a woman's response to fertility treatments, based on the measurement of AMH level in said woman.

AMH is a glycoprotein of 140 kDa belonging to the transforming growth factor β family (TGFβ), that is expressed only in the gonads. It was originally identified in connection with its role in male fetal sex differentiation during embryonic development, but later studies have shown that AMH exerts inhibitory effects on the development and function of reproductive organs in both sexes. In the ovary, AMH expression is restricted to a single cell type, i.e. granulosa cells (Vigier et al., 1984, Endocrinology 114: 1315-1320; Takahashi et al., 1986, Biol Reprod 35: 447-453). AMH expression is the highest in granulosa cells of preantral and small antral follicles, decreases during terminal follicular growth, and low AMH concentrations have been found in follicular fluid of large antral and preovulatory follicles (Monniaux et al., 2008, Biol Reprod 79: 387-396). This pattern of expression in granulosa cells of growing follicles makes AMH an ideal marker for the size of the ovarian follicle pool. The inventors have previously observed that in cow, as in human, plasma concentration of AMH is a good marker of the status of the follicular population able to respond to FSH (follicle-stimulating hormone) treatment and to ovulate (Rico et al., 2009, Biol Reprod 80: 50-59).

Ovulation is a first step that is necessary but not sufficient to obtain fertilizable oocytes and transferable embryos. The other steps, concerning survival of the ovulated oocyte in the oviduct, transit and survival of sperm in the female genital tract after insemination, fertilization and early embryo development up to the morula or the blastocyst stage, are also decisive for production of good quality oocytes and embryos. Previous results have shown that superovulation can decrease developmental competence of bovine oocytes (Lonergan et al., 1994, Mol Reprod Dev 37: 48-53; Blondin et al., 1996, Theriogenology 46: 1191-1203) and that a high ovulation capacity can sometime produce a low proportion of transferable embryos (Ireland et al., 2007, Human Reprod 22: 1687-1695). These results might be explained by a poor synchronization between ovulation and insemination timing, or by abnormal endocrine profiles of steroids that can affect both sperm transport and embryo development and survival in the case of multiple ovulations (Greve and Callesen, Reprod Nutr Dev 41: 451-459). Due to the multiplicity of hormones, growth factors and cell-cell interactions influencing the number and the quality of oocytes and embryos, up to now, there is no reliable method able to predict the number of fertilizable oocytes and transferable embryos that can be produced by a potential donor cow after superovulatory treatment.

Now, the inventors found out that AMH concentration in plasma could be not only an endocrine marker of follicular population, but also a faithful predictive marker of the numbers of transferable embryos or fertilizable oocytes able to be produced by an individual animal after superovulatory treatment. The present invention proposes, for the first time, a prognosis method to determine the capacity of embryo or oocyte production by potential embryo or oocyte donor animals, from the result of measurement of AMH concentration in a biological sample of these potential donors. The inventors showed that plasma or serum AMH concentration can stay stable in individual animals over several months, and this property makes this prognosis to be performed by only one blood test per animal.

In the first aspect, the present invention provides a method to select a non-human female animal subject having the capacity to produce appropriate number of transferable embryos or fertilizable oocytes in said animal, said method comprising the determination of the anti-Mullerian hormone concentration in a biological sample before an ovarian superovulatory treatment.

In the context of the present invention, "appropriate number of transferable embryos or fertilizable oocytes" should be understood as at least 10 transferable embryos, or at least 10 fertilizable oocytes.

The transferable embryos are those qualified as "good" embryos, according to the classic morphological standard of shape and color used in field work (Callesen et al., 1995, J Anim Sci 73: 1539-1543) and the definitions developed by the International Embryo Transfer Society. According to the invention, production of embryos or oocytes is achieved according to techniques well-known in prior art. An embryo donor animal which can produce more than 10 transferable embryos after a superovulatory treatment is defined as a good embryo donor. An embryo donor which produces less than 5 transferable embryos is defined as a poor embryo donor.

The fertilizable oocytes are the oocytes collected from the follicles of a female animal, which are capable to be fertilized in vitro and to give rise to transferable embryos.

The embryos can be produced by in vivo fertilization through a natural or artificial insemination of a female animal which has formerly received an ovarian superovulatory treatment. Embryos produced in this way are collected through genital tract. The embryos can be also produced by in vitro fertilization of oocytes collected by follicular puncture (Ovum Pick-Up technique, or OPU) from the ovaries of a female animal which has formerly received an ovarian superovulatory treatment. Oocytes (immature ova) are collected from the follicles in the ovaries by aspiration using ultrasonic guidance through the vaginal wall. The oocytes are matured in the laboratory for 24 hours then fertilized and embryos are cultured for a further seven-day period before being transferred to prepared recipients or frozen for use at a later date.

In a particular embodiment, the method according to the present invention comprises the following steps:
a) sampling of a biological sample,
b) measuring in said biological sample the anti-Mullerian hormone concentration,
c) comparing said concentration with two, respectively "high" and "low", reference values
and wherein if the anti-Mullerian hormone concentration is greater than the "high" reference value, then the animal is considered as having a good capacity to produce transferable embryos or fertilizable oocytes; conversely, if the anti-Mullerian hormone concentration is lower than the "low" reference value, then the animal is considered as having a poor capacity to produce transferable embryos or fertilizable oocytes.

The said biological sample can be any biological fluids selected from the group comprising plasma, serum, milk, urine or saliva.

In a preferred embodiment according to the invention, the said biological sample is plasma or serum.

According to the invention, the AMH concentrations can be measured by any classical dosage method disclosed in literature or known by the skilled person.

In another preferred embodiment of the present invention, the animal is a ruminant.

In a more preferred embodiment of the present method according to the invention, the ruminant is selected from the group comprising bovine and caprine species.

The term "reference value" is used in the present invention to define a threshold concentration of AMH over (for the "high" reference) or under (for the "low" reference) which an appropriate or unappropriate number of transferable embryos or fertilizable oocytes is respectively predicted to be recovered from a donor animal with a confidence level statistically higher than 95%. These reference values have been determined from statistic analysis of a number of measurements of both AMH concentrations and numbers of embryos produced in different subjects.

According to the present invention, the "high" reference value of anti-Mullerian hormone concentration in plasma of bovine species is comprised between 160 pg/ml to 200 pg/ml, preferably 180 pg/ml for production of more than 10 transferable embryos or fertilizable oocytes per ovarian superovulatory treatment, and the "low" reference value of anti-Mullerian hormone concentration in plasma of bovine species is comprised between 80 pg/ml to 110 pg/ml, preferably 90 pg/ml for production of less than 5 transferable embryos or fertilizable oocytes per ovarian superovulatory treatment.

In the second aspect, the present invention is also directed to the use of anti-Mullerian hormone as a predictive marker of the number of transferable embryos or fertilizable oocytes able to be produced in a non-human female animal subject.

The invention is illustrated by the following examples and FIGS. 1 to 5.

EXAMPLE 1

AMH Concentration in Plasma and Production of Embryos after Superovulation in Prim'Holstein×Normande Cows Materials and Methods
Animals and Experimental Design Forty-five crossbred Prim'Holstein×Normande dairy cows, 2 to 4 years old, were submitted to a blood test during their first lactation, between 60 and 90 days after calving, to determine their AMH concentration in plasma. Blood (2 to 4 ml) was collected in an heparinized tube, then plasma was recovered after centrifugation and stored at −20° C. until AMH assay.

Afterwards, these cows were submitted to repeated ovarian superovulatory treatments (1 to 9 repetitions of treatments per animal, mean number of repetitions per animal=5.4), each followed by artificial insemination and embryo collect. Each superovulatory treatment consisted in administration of 32 mg of FSH (follicle-stimulating hormone, STIMOFUL®), given as twice daily injections over 4 days on a standard decreasing dose schedule (Mapletoft et al., 2002, Reprod Nutr Dev 42: 601-611). The interval between blood recovery during lactation and the first embryo collect varied in the range of [3-30] months between cows (mean interval=17.2 months). Embryos were collected by flushing uterine horns, counted and their quality was evaluated according to classic morphological criteria (Callesen et al., 1995, J Anim Sci 73: 1539-1543). Embryos with quality 1 to 3 according to the criteria of Callesen et al. (1995) were defined as transferable (i.e. good) embryos.

AMH Assay

AMH was measured with the Active MIS/AMH ELISA kit (Beckman Coulter France, Roissy CDG, France) as previously described (Monniaux et al., 2008, Biol Reprod 79: 387-396). AMH was measured on 50 µl of undiluted plasma. AMH concentrations were higher than the limit of detection of the assay (1 pg per well, corresponding to 0.020 ng/ml in plasma samples) in all the plasmas tested. Intra-assay coefficient of variation was found to be 11.8% and 3.6% for plasma samples containing 0.033 ng/ml and 0.125 ng/ml AMH concentration, respectively.

Results

Figure 1:
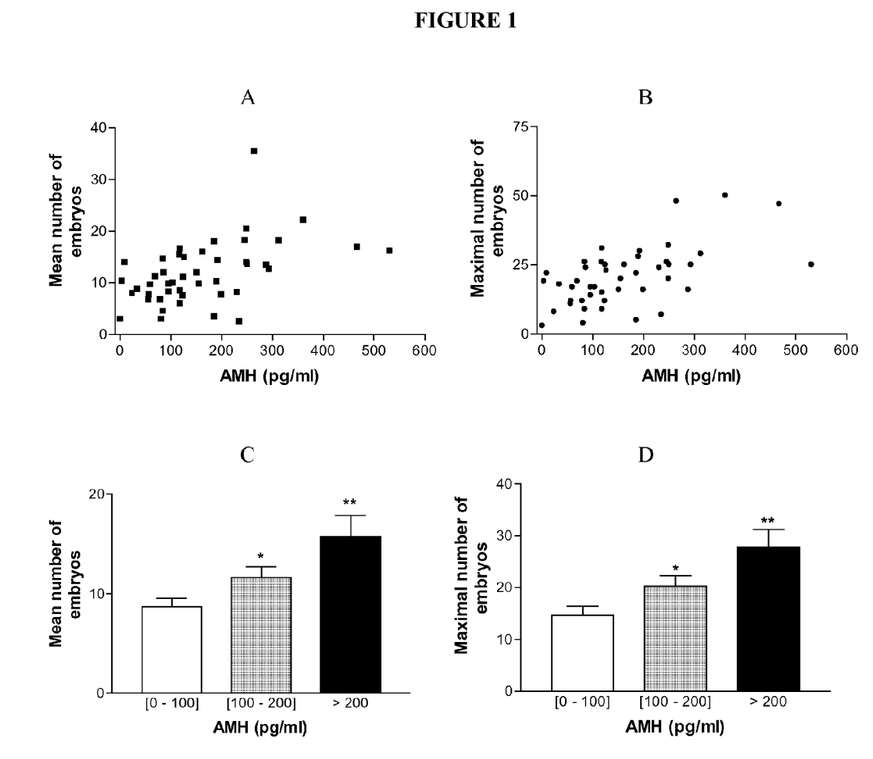
FIG. 1A illustrates the relationship between the average number of embryos produced per female and their AMH concentration in plasma ($r=0.49$, $p<0.001$). Blood sample for each 45 cows was taken during their first lactation and then these cows have been submitted to ovarian superovulatory treatment, artificial insemination and embryo collect.
FIG. 1B illustrates the relationship between the maximal number of embryos produced per female and their AMH concentration in plasma ($r=0.58$, $p<0.0001$). Blood sample for each 45 cows was taken during their first lactation and then these cows have been submitted to ovarian superovulatory treatment, artificial insemination and embryo collect.
FIG. 1C illustrates the relationship between AMH concentration in plasma and the average number of embryos produced per female. 45 cows were divided into three groups according to their AMH concentration, group [0-100] (n=16), group [100-200] (n=15) and group [>200] (n=14). *$p<0.05$, **$p<0.01$ vs. group [0-100].
FIG. 1D illustrates the relationship between AMH concentration in plasma and the maximal number of embryos produced per female. 45 cows were divided into three groups according to their AMH concentration in plasma, as defined in legend of FIG. 1C. *$p<0.05$, **$p<0.01$ vs. group [0-100].

A close positive correlation was observed between AMH concentration measured in plasma of cows during their first lactation and the average and maximal number of embryos collected per animal (r=0.49, p<0.001 and r=0.58, p<0.0001, respectively, FIGS. 1A and 1B). The allocation of animals to 3 groups according to their AMH concentration discloses that the animals having AMH concentration between 100 to 200 pg/ml and higher than 200 pg/ml have produced higher numbers of embryos than the animals having less than 100 pg/ml of AMH (group [100-200] vs. group [0-100], p<0.05; group [>200] vs. group [0-100], p<0.01 for both average and maximal number of embryos, FIGS. 1C and 1D).

Figure 2:
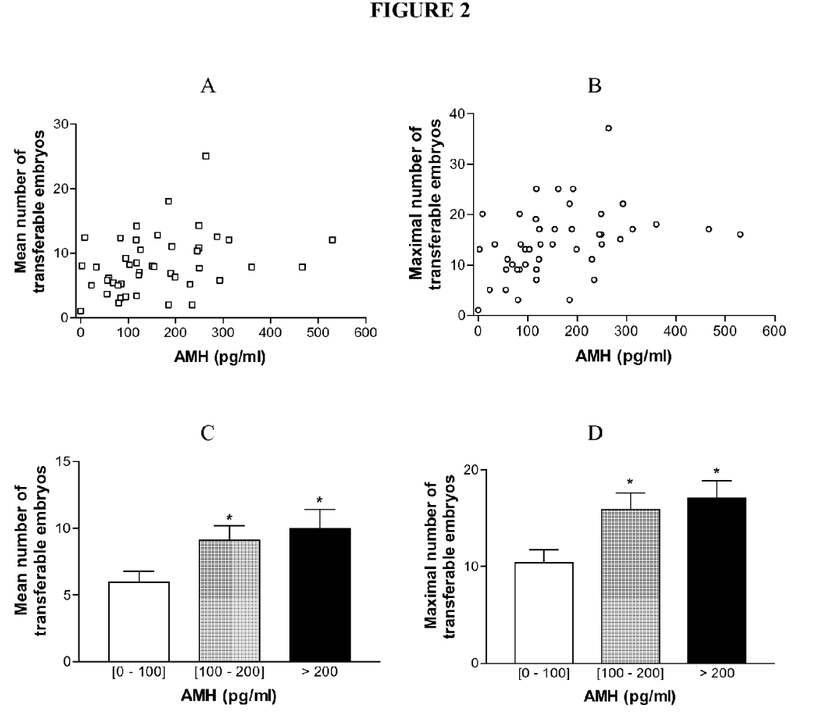
FIG. 2A illustrates the relationship between the average number of transferable embryos produced per female and their AMH concentration in plasma ($r=0.32$, $p<0.05$). Blood sample for each 45 cows was taken during their first lactation and then these cows have been submitted to ovarian superovulatory treatment, artificial insemination and embryo collect.
FIG. 2B illustrates the relationship between the maximal number of transferable embryos produced per female and their AMH concentration in plasma ($r=0.38$, $p=0.01$). Blood sample for each 45 cows was taken during their first lactation and then these cows have been submitted to ovarian superovulatory treatment, artificial insemination and embryo collect.
FIG. 2C illustrates the relationship between AMH concentration in plasma and the average number of transferable embryos produced per female. 45 cows were divided into three groups according to their AMH concentration, as defined in legend of FIG. 1C. *$p<0.05$ vs. group [0-100].
FIG. 2D illustrates the relationship between AMH concentration in plasma and the maximal number of transferable embryos produced per female. 45 cows were divided into three groups according to their AMH concentration, as defined in legend of FIG. 1C. *$p<0.05$, vs. group [0-100].

The average and maximal numbers of transferable embryos collected per animal were also correlated to AMH concentration measured in plasma of cows during their first lactation (r=0.32, p<0.05 and r=0.38, p=0.01, respectively, FIGS. 2A and 2B). The allocation of animals to 3 groups according to their AMH concentration shows that the animals having AMH concentration between 100 to 200 pg/ml and higher than 200 pg/ml have produced higher numbers of transferable embryos than the animals having less than 100 pg/ml of AMH (group [100-200] vs. group [0-100], p<0.05; group [>200] vs. group [0-100], p<0.05 for both average and maximal number of transferable embryos, FIGS. 2C and 2D).

Figure 3:
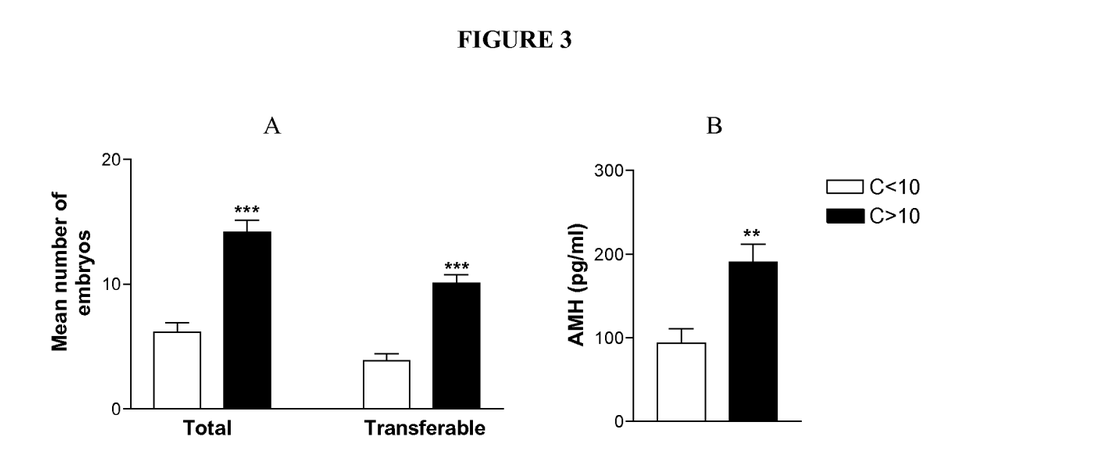
FIG. 3A illustrates mean embryo production (total embryos and transferable embryos) per female. 45 cows were divided in two groups according to their capacity (C) of embryo production, group [C<10] (n=13) and group [C>10] (n=32). Capacity was defined as the maximal number of transferable embryos that could be collected per female after superovulatory treatment. ***p<0.001 vs. group [C<10].
FIG. 3B illustrates mean AMH concentration in plasma. 45 cows were divided in two groups according to their capacity (C) of embryo production, as defined in legend of FIG. 3A. **p<0.01 vs. group [C<10].

In a further analysis, animals were allocated to 2 groups according to their capacity of production of transferable embryos. This capacity (C) was defined as the maximal number of transferable embryos that could be collected per animal after superovulatory treatment. Animals with a high capacity of production of transferable embryos (good embryo donors, C>10) had higher AMH concentrations measured in plasma during their first lactation (p<0.01, FIG. 3B), and they produced also a higher average number of total embryos (p<0.001) and transferable embryos (p<0.001, FIG. 3A) than embryo donors with C<10. Moreover, the good embryo donors were able to produce in average 5 times more transferable embryos compared with poor embryo donors (donors with C<5) and had 2.7 times higher AMH concentrations than the poor embryo donors in plasma during their first lactation.

In subsequent analyses, data modelling was carried out using different linear and non-linear models and best fitting was found using polynomial regression models. With these models and the present data, the choice of a low reference value of AMH concentrations comprised between 80 and 110 pg/ml allowed discarding 70% of poor embryo donors among the population of poor embryo donors, and the choice of a high reference value of AMH concentrations comprised between 160 and 200 pg/ml allowed selecting 60% of good embryo donors among the population of good embryo donors.

EXAMPLE 2

Repeatability of AMH Concentration in Plasma and Follicular Response in Prim'Holstein Cows after Superovulation and OPU Materials and Methods
Animals and Experimental Design Thirteen Prim'Holstein cows were submitted to repeated ovarian superovulatory treatments, each followed by OPU on the large follicles (diameter>6 mm) that were detected by ovarian ultrasonography. Each superovulatory treatment consisted in administration of 32 mg of FSH (STIMOFUL®), given as twice daily injections over 4 days on a decreasing dose schedule and follicles were punctioned 48h after the last FSH injection. At each repetition of treatment, blood (2 to 4 ml) was collected in an heparinized tube just before the first FSH injection (before treatment) and at the day of OPU (at OPU), then plasma was recovered after centrifugation and stored at −20° C. until AMH assay.

Cows entered the experimental protocol in January (6 cows), March (4 cows) or May (3 cows). Then animals were treated and submitted to OPU repeatedly (between 4 and 11 repetitions per cow) until December. No treatment and OPU was carried out on cows during the hot season (July and August). Five cows with low follicular response (<15 large follicles at each punction) left the protocol within 3 months only after entry.

AMH Assay

AMH concentration was measured in plasma with the Active MIS/AMH ELISA kit (Beckman Coulter France, Roissy CDG, France), as previously described in example 1.

Data Analysis

For group comparisons, data were analyzed using t-test or one-way ANOVA. In order to evaluate a seasonal effect, 5 periods of time were compared: January-February, March-April, May-June, September-October and November-December. The effects of repetition of treatments on the number of large follicles and AMH concentrations were analyzed with repeated measures ANOVA. The repeatability of each parameter was calculated as the ratio of the between-animal variance to the sum of the between-animal and the residual variances. For correlation studies, the significance of the value of the correlation coefficient was considered according to the Bravais-Pearson-r critical values. For all analyses, differences with $p>0.05$ were considered as not significant.

Results

A total number of 90 treatments, each followed by OPU, were carried out on the 13 cows. AMH concentrations increased following treatment (176.6±11.8 vs. 253.7±19.8 pg/ml, AMH before treatment vs. AMH at OPU, $p<0.01$) and a highly significant correlation was observed between AMH concentrations measured before treatment and at the time of OPU ($r=0.88$, $p<0.0001$). The number of large follicles at OPU was significantly correlated with AMH concentrations before treatment ($r=0.56$, $p<0.0001$) and at the time of OPU (0.65, $p<0.0001$).

No seasonal effect was observed for both the number of large follicles on ovaries at OPU and AMH concentrations. For all parameters, there was a tendency to an increase through time, likely related to the early exit of 5 low responding animals from the experimental protocol as said above, but this tendency was not significant (Table 1).

Figure 4:
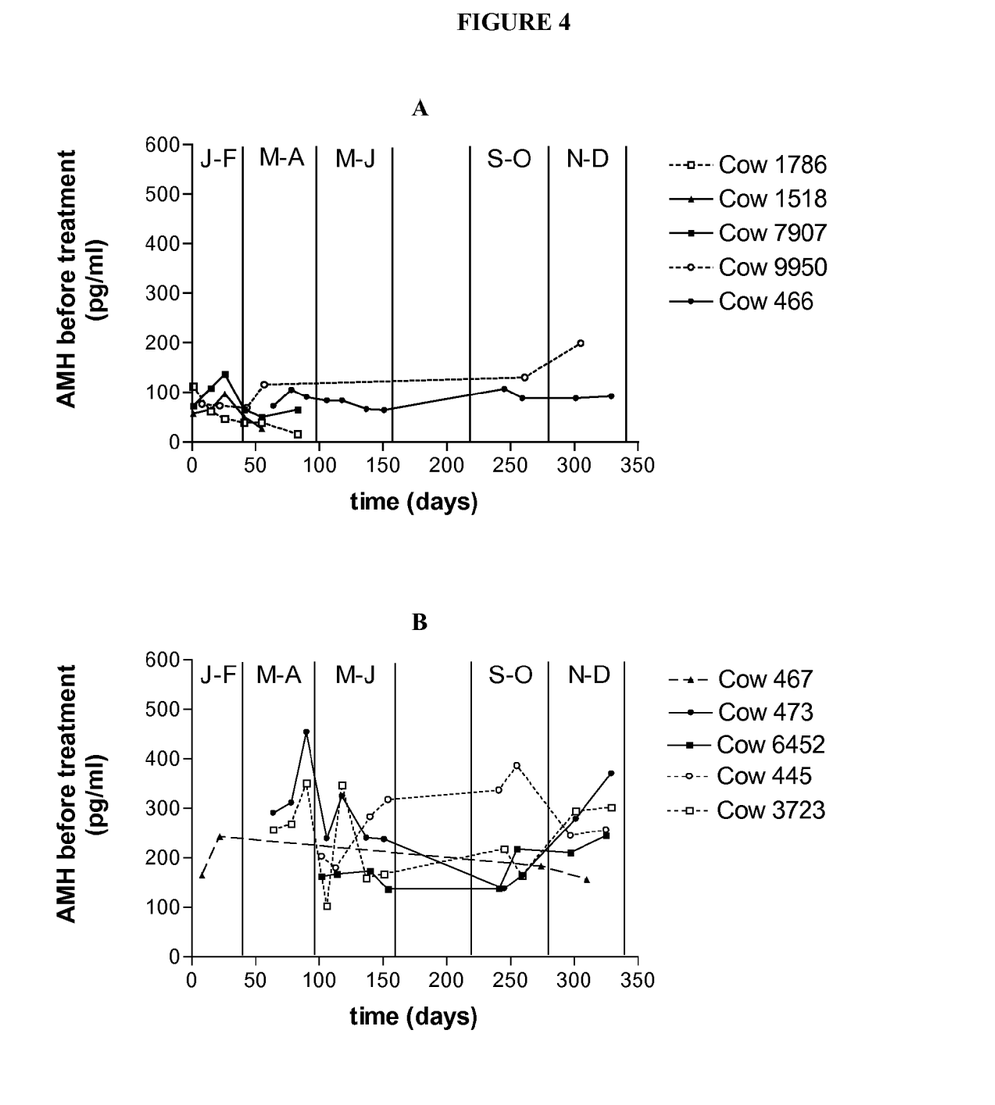
FIG. 4A illustrates individual variations in AMH concentrations of 5 cows with low mean AMH concentrations (<150 pg/ml), measured before each repetition of ovarian superovulatory treatment and OPU (Ovum Pick-Up).
FIG. 4B illustrates individual variations in AMH concentrations of 5 cows with high mean AMH concentrations (>150 pg/ml), measured before each repetition of ovarian superovulatory treatment and OPU.
Figure 5:
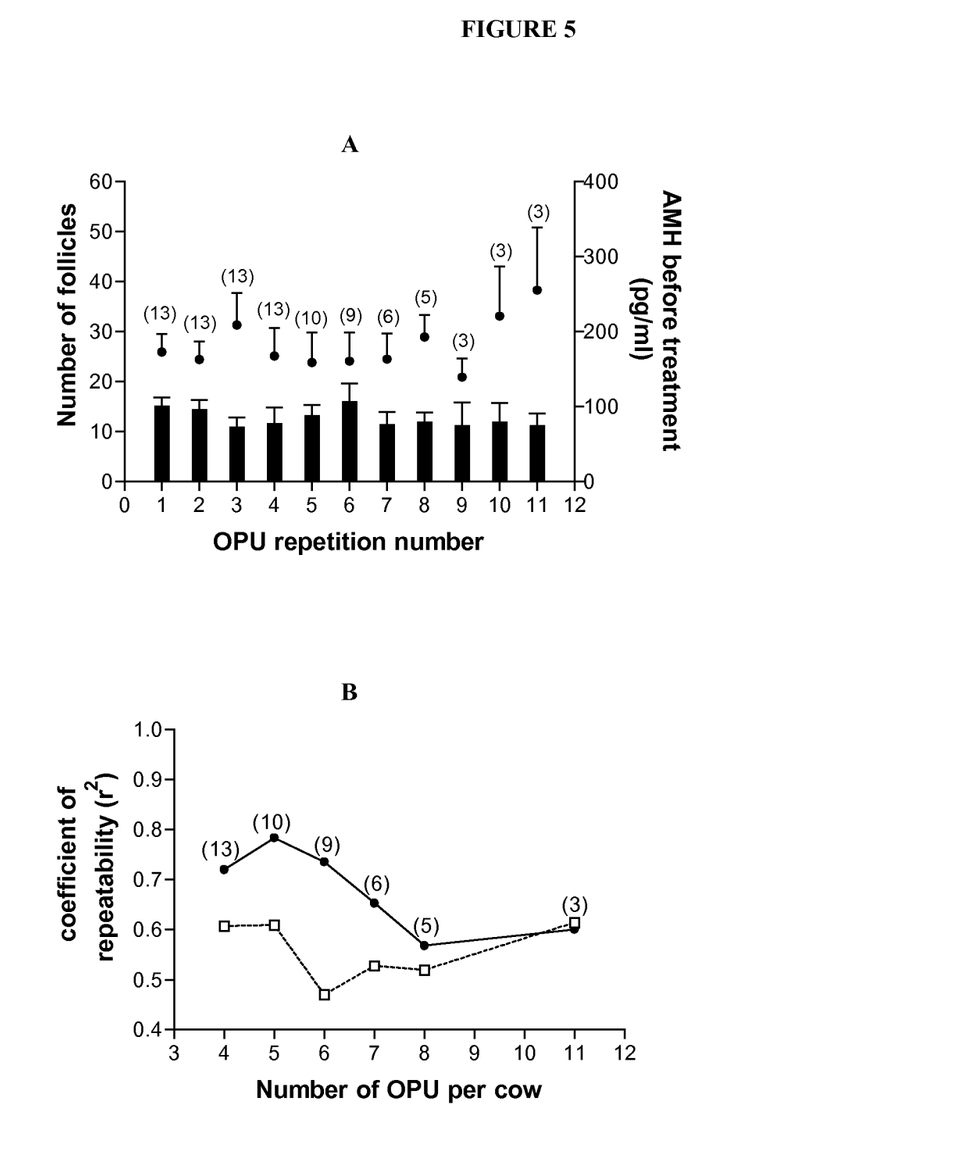
FIG. 5A illustrates the effect of OPU repetitions on AMH concentrations before treatment (black circles, right scale) and on the number of large follicles at OPU (black bars, left scale). Cows were treated repeatedly (n=4 to 11 repetitions per cow). The horizontal axis represents the OPU repetition number. The number of studied cows is indicated between brackets.
FIG. 5B illustrates the value of the coefficient of repeatability of AMH concentration before treatment (black circles) and of the number of large follicles at OPU (empty squares). Cows were treated repeatedly (n=4 to 11 repetitions per cow). The horizontal axis represents the number of OPU that were carried out per cow. The number of studied cows is indicated between brackets.

AMH concentrations before treatment showed low intra-animal variations with time (FIGS. 4A and 4B). FIG. 5A and FIG. 5B illustrate individual repeatability of AMH concentrations before treatment and follicle numbers at OPU during the repeated sessions of OPU. There was no significant effect of the OPU repetition number on the number of large follicles on ovaries at OPU and AMH concentrations before treatment (FIG. 5A). When data were analyzed for 4 (n=13 cows), 5 (n=10 cows), 6 (n=9 cows), 7 (n=6 cows), 8 (n=5 cows) or 11 repeated OPU (n=3 cows), highly significant repeatability was observed in all analyses for AMH concentrations before treatment ($p<0.0001$) (FIG. 5B). Similar results were observed for AMH concentrations at the time of OPU (data not shown).

TABLE 1

Effect of season on AMH concentrations before superovulatory treatment and at OPU and on the number of large follicles at OPU

| Period of time | J-F | M-A | M-J | J-A | S-O | N-D |
|---|---|---|---|---|---|---|
| Number of cows | 6 | 8 | 7 | 0 | 8 | 8 |
| AMH before treatment (pg/ml) | 126.1 ± 28.5 | 136.6 ± 42.4 | 182.5 ± 29.6 | NA | 229.0 ± 52.3 | 256.4 ± 44.3 |
| AMH at OPU (pg/ml) | 164.3 ± 34.1 | 176.4 ± 59.7 | 257.2 ± 46.8 | NA | 417.5 ± 101.8 | 340.5 ± 63.8 |
| Number of large follicles at OPU | 11.75 ± 2.26 | 11.65 ± 2.03 | 14.19 ± 2.52 | NA | 12.19 ± 2.76 | 16.00 ± 3.70 |

The invention claimed is:

1. A method for predicting a number of transferable embryos or fertilizable oocytes able to be produced by an individual non-human female animal subject after superovulatory treatment, said method comprising:
   a) determining an anti-Mullerian hormone concentration in a blood sample before an ovarian superovulatory treatment by measuring the anti-Mullerian hormone concentration in the blood sample; and
   b) comparing said concentration with a reference value, wherein if the measured anti-Mullerian hormone concentration is greater than the reference value, then the animal is considered as having a good capacity to produce transferable embryos or fertilizable oocytes; and wherein the reference value in the plasma of bovine species is between 100 and 200 pg/ml for production of more than 10 transferable embryos per ovarian superovulatory treatment.

2. The method of claim 1 wherein the anti-Mullerian hormone concentration is measured by employing an ELISA assay.

3. A method for predicting a number of transferable embryos or fertilizable oocytes able to be produced by a non-human female animal after superovulatory treatment, said method comprising:
   a) determining an anti-Mullerian hormone concentration in a blood sample of the animal before an ovarian superovulatory treatment, by measuring the anti-Mullerian hormone concentration in the blood sample; and
   b) comparing said concentration with two, respectively "high" and "low," reference values and wherein if the anti-Mullerian hormone concentration is greater than the "high" reference value, then the animal is considered as having a good capacity to produce transferable embryos or fertilizable oocytes; conversely, if the anti-Mullerian hormone concentration is lower than the "low" reference value, then the animal is considered as having a poor capacity to produce transferable embryos or fertilizable oocytes, wherein the animal is a ruminant of the bovine species and the "high" reference value of anti-Mullerian hormone concentration in plasma of bovine species is between 160 pg/ml to 200 pg/ml for production of more than 10 transferable embryos or fertilizable oocytes per ovarian superovulatory treatment, and the "low" reference value of anti-Mullerian hormone concentration in plasma of bovine species is between 80 pg/ml to 110 pg/ml, for production of less than 5 transferable embryos or fertilizable oocytes per ovarian superovulatory treatment.

4. The method of claim 3 wherein the anti-Mullerian hormone concentration is measured in plasma by employing an ELISA assay.

5. The method of claim 3 wherein the animal is a ruminant of the bovine species and the "high" reference value of anti-Mullerian hormone concentration in plasma of bovine species is 180 pg/ml for production of more than 10 transferable embryos or fertilizable oocytes per ovarian superovulatory treatment, and the "low" reference value of anti-Mullerian hormone concentration in plasma of bovine species is 90 pg/ml, for production of less than 5 transferable embryos or fertilizable oocytes per ovarian superovulatory treatment.

6. The method of claim 5 wherein the anti-Mullerian hormone concentration is measured in plasma by employing an ELISA assay.

7. A method for improving the number of transferable embryos produced in non-human female animals which comprises the steps of:
  (a) determining an anti-Mullerian hormone concentration in a blood sample of each of the non-human female animals before an ovarian superovulatory treatment by measuring the anti-Mullerian hormone concentration in the blood sample,
  (b) comparing said concentration with a reference value, wherein if the measured anti-Mullerian hormone concentration is greater than the reference value, then the animal is considered as having a good capacity to produce transferable embryos or fertilizable oocytes and wherein the reference value in the plasma of bovine species is between 100 and 200 pg/ml for production of more than 10 transferable embryos per ovarian superovulatory treatment;
  (c) administering superovulatory treatment to only those non-human female animals wherein the anti-Mullerian hormone concentration is greater than the reference value of anti-Mullerian hormone concentration indicating the animal has a good capacity to produce transferable embryos or fertilizable oocytes;
  (d) artificially inseminating the non-human female animals to which superovulatory treatment was administered; and
  (e) obtaining transferable embryos.

8. The method of claim 7 further comprising the step of obtaining a blood sample from the non-human female animal subjects for determination of the anti-Mullerian hormone concentration in the blood sample.

9. The method of claim 7 wherein the animal is of the bovine species and the blood sample is plasma or serum.

10. The method of claim 7 wherein comparing said concentration with a reference value comprises comparing said concentration with two, respectively "high" and "low," reference values and wherein if the anti-Mullerian hormone concentration is greater than the "high" reference value, then the animal is considered as having a good capacity to produce transferable embryos or fertilizable oocytes; conversely, if the anti-Mullerian hormone concentration is lower than the "low" reference value, then the animal is considered as having a poor capacity to produce transferable embryos or fertilizable oocytes, wherein the animal is a ruminant of the bovine species and the "high" reference value of anti-Mullerian hormone concentration in plasma of bovine species is between 160 pg/ml to 200 pg/ml for production of more than 10 transferable embryos or fertilizable oocytes per ovarian superovulatory treatment, and the "low" reference value of anti-Mullerian hormone concentration in plasma of bovine species is between 80 pg/ml to 100 pg/ml, for production of less than 5 transferable embryos or fertilizable oocytes per ovarian superovulatory treatment.

11. The method of claim 7 wherein the anti-Mullerian hormone concentration is measured by employing an ELISA assay.

12. A method for improving the number of fertilizable oocytes produced in non-human female animals which comprises the steps of:
  (a) determining an anti-Mullerian hormone concentration in a blood sample of each of the non-human female animals before an ovarian superovulatory treatment by measuring the anti-Mullerian hormone concentration in the blood sample,
  (b) comparing said concentration with a reference value, wherein if the measured anti-Mullerian hormone concentration is greater than the reference value, then the animal is considered as having a good capacity to produce transferable embryos or fertilizable oocytes and wherein the reference value in the plasma of bovine species is between 100 and 200 pg/ml for production of more than 10 transferable embryos per ovarian superovulatory treatment;
  (c) administering superovulatory treatment to only those non-human female animals wherein the anti-Mullerian hormone concentration is greater than the reference value of anti-Mullerian hormone concentration indicating the animal has a good capacity to produce transferable embryos or fertilizable oocytes; and
  (d) recovering fertilizable oocytes from the ovaries of the non-human female animals to which superovulatory treatment was administered.

13. The method of claim 12 further comprising the step of subjecting recovered fertilizable oocytes to in vitro fertilization.

14. The method of claim 12 further comprising the step of obtaining a blood sample from the non-human female animal subjects for determination of the anti-Mullerian hormone concentration in the blood sample.

15. The method of claim 12 wherein the animal is of the bovine species and the blood sample is plasma or serum.

16. The method of claim 12 wherein the anti-Mullerian hormone concentration is measured by employing an ELISA assay.

17. The method of claim 12 wherein comparing said concentration with a reference value comprises comparing said concentration with two, respectively "high" and "low," reference values and wherein if the anti-Mullerian hormone concentration is greater than the "high" reference value, then the animal is considered as having a good capacity to produce transferable embryos or fertilizable oocytes; conversely, if the anti-Mullerian hormone concentration is lower than the "low" reference value, then the animal is considered as having a poor capacity to produce transferable embryos or fertilizable oocytes, wherein the animal is a ruminant of the bovine species and the "high" reference value of anti-Mullerian hormone concentration in plasma of bovine species is between 160 pg/ml to 200 pg/ml for production of more than 10 transferable embryos or fertilizable oocytes per ovarian superovulatory treatment, and the "low" reference value of anti-Mullerian hormone concentration in plasma of bovine species is between 80 pg/mi to 110 pg/mi, for production of less than 5 transferable embryos or fertilizable oocytes per ovarian superovulatory treatment.

* * * * *

UNITED STATES PATENT AND TRADEMARK OFFICE
CERTIFICATE OF CORRECTION

| | | |
|---|---|---|
| PATENT NO. | : 8,758,219 B2 | Page 1 of 1 |
| APPLICATION NO. | : 13/140394 | |
| DATED | : June 24, 2014 | |
| INVENTOR(S) | : Danielle Monniaux-Jaudet, Stéphane Fabre and Rozenn Dalbies-Tran | |

It is certified that error appears in the above-identified patent and that said Letters Patent is hereby corrected as shown below:

In the Claims:

In claim 3, column 8, line 61, please replace "vulatory treatment, by measuring" with -- vulatory treatment by measuring --

In claim 17, column 11, line 8, please replace "between 80 pg/mi to 110 pg/mi" with -- between 80 pg/ml to 110 pg/ml --

Signed and Sealed this
Thirtieth Day of September, 2014

Michelle K. Lee
*Deputy Director of the United States Patent and Trademark Office*